(12) United States Patent
Horn et al.

(10) Patent No.: US 8,048,028 B2
(45) Date of Patent: Nov. 1, 2011

(54) REINFORCED MEDICAL BALLOON

(75) Inventors: Daniel J. Horn, Shoreview, MN (US); John Jianhua Chen, Plymouth, MN (US); Jan Weber, Maple Grove, MN (US); Thomas J. Holman, Princeton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 908 days.

(21) Appl. No.: 11/060,093

(22) Filed: Feb. 17, 2005

(65) Prior Publication Data
US 2006/0184112 A1 Aug. 17, 2006

(51) Int. Cl.
*A61M 25/10* (2006.01)

(52) U.S. Cl. .................................. 604/103.08

(58) Field of Classification Search ............... 604/103.6, 604/103.8
See application file for complete search history.

(56) References Cited

U.S. PATENT DOCUMENTS

| | | | |
|---|---|---|---|
| 4,941,877 A * | 7/1990 | Montano, Jr. ............ 604/103.07 |
| 4,963,313 A | 10/1990 | Noddin et al. |
| 4,976,590 A | 12/1990 | Baldwin |
| 4,976,690 A | 12/1990 | Solar et al. |
| 5,156,594 A | 10/1992 | Keith |
| 5,195,969 A | 3/1993 | Wang et al. |
| 5,545,132 A * | 8/1996 | Fagan et al. ............... 604/103.08 |
| 5,593,419 A | 1/1997 | Segar |
| 5,674,242 A | 10/1997 | Phan et al. |
| 5,714,110 A | 2/1998 | Wang et al. |
| 5,725,570 A | 3/1998 | Heath |
| 5,733,301 A * | 3/1998 | Forman .................... 606/192 |
| 5,826,588 A * | 10/1998 | Forman .................... 128/898 |
| 6,010,480 A | 1/2000 | Abele et al. |
| 6,071,273 A | 6/2000 | Euteneuer et al. |
| 6,120,364 A | 9/2000 | Laflamme |
| 6,146,356 A * | 11/2000 | Wang et al. ............... 604/96.01 |
| 6,528,150 B2 * | 3/2003 | Nazarova et al. ........... 428/212 |
| 6,545,097 B2 | 4/2003 | Pinchuk et al. |
| 6,712,807 B2 | 3/2004 | Stivland et al. |
| 6,736,841 B2 * | 5/2004 | Musbach et al. ............ 623/1.11 |
| 6,786,889 B1 * | 9/2004 | Musbach et al. .......... 604/103.08 |
| 7,252,650 B1 * | 8/2007 | Andrews et al. ......... 604/103.06 |
| 7,479,128 B1 * | 1/2009 | Lenz ........................ 604/265 |
| 2002/0082679 A1 * | 6/2002 | Sirhan et al. ............... 623/1.15 |
| 2003/0003220 A1 | 1/2003 | Zhong et al. |
| 2003/0018380 A1 | 1/2003 | Craig et al. |

(Continued)

FOREIGN PATENT DOCUMENTS
EP 1 388 346 2/2004
WO WO 2005/112845 12/2005

OTHER PUBLICATIONS

International Search Report received in International application No. PCT/US2006/005400, mailed Jun. 22, 2006.

(Continued)

*Primary Examiner* — Nicholas D Lucchesi
*Assistant Examiner* — Aarti B Berdichevsky
(74) *Attorney, Agent, or Firm* — Seager, Tufte & Wickhem, LLC

(57) ABSTRACT

The invention relates to medical balloons, and methods of modifying said balloons by forming a void pattern in their exterior surfaces and filling the voids with a material, such as a fiber or a nanomaterial (e.g., nanotubes, such as carbon nanotubes) and a matrix material, e.g., a polymer.

15 Claims, 7 Drawing Sheets

U.S. PATENT DOCUMENTS

| | | |
|---|---|---|
| 2003/0055378 A1 | 3/2003 | Wang et al. |
| 2003/0065355 A1 | 4/2003 | Weber |
| 2003/0093107 A1 | 5/2003 | Parsonage et al. |
| 2003/0099798 A1 | 5/2003 | George et al. |
| 2003/0143350 A1 | 7/2003 | Jimenez |
| 2003/0163148 A1 | 8/2003 | Wang et al. |
| 2003/0185895 A1 | 10/2003 | Lanphere et al. |
| 2003/0229184 A1 | 12/2003 | Acquarulo, Jr. et al. |
| 2004/0068285 A1 | 4/2004 | Burgmeier et al. |
| 2004/0078052 A1 | 4/2004 | St. Pierre et al. |
| 2004/0087902 A1 | 5/2004 | Richter |
| 2004/0131808 A1 | 7/2004 | Schoenle et al. |
| 2004/0133223 A1 | 7/2004 | Weber |
| 2004/0138733 A1 | 7/2004 | Weber et al. |
| 2005/0043679 A1 | 2/2005 | Devens, Jr. et al. |
| 2005/0043712 A1 | 2/2005 | Devens, Jr. |
| 2005/0149102 A1 | 7/2005 | Radisch, Jr. et al. |
| 2006/0182873 A1 | 8/2006 | Klisch et al. |

OTHER PUBLICATIONS

Ali, A., *"Carbon Nanotube Reinforced Carbon Nano Composite Fibrils by Electro-Spinning"*, Thesis submitted to Drexel University, Oct. 2002.

Bahr, J. et al., "Functionalization of Carbon Nanotubes by Electrochemical Reduction of Aryl Diazonium Salts: A Bucky Paper Electrode", *J. Am. Chem. Soc.*, 2001, 123, 6536-6542.

Bandyopadhyaya, R. et al., "Stabilization of Individual Carbon Nanotubes in Aqueous Solutions", *Nano Letters*, vol. 2(1), 2002, 25-28.

Bronikowski, M.J. et al., "Gas-Phase Production of Carbon Single-Walled Nanotubes from Carbon Monoxide via the HiPco Process: A Parametric Study", *J. Vac. Sci. Technol.* A 19(4), Jul./Aug. 2001, 1800-1805.

Davis, V.A. et al., "Phase Behavior and Rheology of SWNTs in Superacids", *Macromolecules* 2004, 37, 154-160.

Fennessey, S.F. et al., "Fabrication of Aligned and Molecularly Oriented Electrospun Polyacrylonitrile Nanofibers and the Mechanical Behavior of Their Twisted Yarns", *Polymer* 25 (2004), 4217-4225.

Guo, Y. et al., "Manipulation of Single-Wall Carbon Nanotubes into Aligned Molecular Layers", *Chemical Physics Letters* 362 (2002), 314-318.

Guo, Y. et a., "Multi-layer LB Films of Single-Wall Carbon Nanotubes", *Physica B* 323 (2002), 235-236.

Huang, Z. et al., "A Review on Polymer Nanofibers by Electrospinning and Their Applications in Nanocomposites", *Composites Science and Technology* 63 (2003), 2223-2253.

Ko, F. et al., "Electrospinning of Continuous Carbon Nanotube-Filled Nanofiber Yarns", *Advanced Materials*, vol. 15(14), Jul. 17, 2000, 1161-1163.

Krasheninnikov, A.V. et al., "Ion-Irradiation-Induced Welding of Carbon Nanotubes", *Physical Review B*, vol. 66, 2002, 245403(1-6).

LaPorte, R.J., *"Hydrophilic Polymer Coatings for Medical Devices"*, Technomic Publishing, Inc., Lancaster, PA, 1997.

Mamedov, A.A. et al., "Molecular Design of Strong Single-Wall Carbon Nanotube/Polyelectrolyte Multilayer Composites", *Nature Materials*, vol. 1, Nov. 2002, 190-194.

Meitl, M.A. et al., "Solution Casting and Transfer Printing Single-Walled Carbon Nanotube Films", *Nano Letters*, vol. 4(9), 2004, 1643-1647.

O'Connell, M.J. et al., "Reversible Water-Solubilization of Single-Walled Carbon Nanotubes by Polymer Wrapping", *Chemical Physics Letters*, vol. 342, 2001, 265-271.

Prasse, T. et al., "Electric Anisotropy of Carbon Manofibre/Epoxy Resin Composites Due to Electric Field Induced Alignment", *Composites Science and Technology* 63 (2003), 1835-1841.

Velasco-Santos, C. et al., "Improvement of Thermal and Mechanical Properties of Carbon Nanotube Composites through Chemical Functionalization", *Chem. Mater.* 15, 2003, 4470-4475.

Bertolino, U.S. Appl. No. 10/263,225, filed Oct. 2, 2002.

Shaw, U.S. Appl. No. 10/762,816, filed Jan. 22, 2004.

Chen et al., U.S. Appl. No. 10/849,742, filed May 20, 2004.

Weber et al., U.S. Appl. No. 10/850,085, filed May 20, 2004.

Weber et al., U.S. Appl. No. 10/850,087, filed May 20, 2004.

\* cited by examiner

REINFORCED MEDICAL BALLOON

TECHNICAL FIELD

The invention relates to medical devices, such as, for example, medical balloons, and related methods.

BACKGROUND

The body includes various passageways such as arteries, other blood vessels, and other body lumens. These passageways, such as a coronary artery, sometimes become constricted or blocked, for example, by plaque or by a tumor. When this occurs, the constricted passageway can be widened in an angioplasty procedure using a balloon catheter, which includes a medical balloon carried by a catheter shaft.

In an angioplasty procedure, the balloon catheter can be used to treat a stenosis, or a narrowing of the body vessel, by collapsing the balloon and delivering it to a region of the vessel that has been narrowed to such a degree that fluid (e.g., blood) flow is restricted. The balloon can be delivered to a target site by passing the catheter shaft over an emplaced guidewire and advancing the catheter to the site. In some cases, the path to the site can be rather tortuous and/or narrow. Upon reaching the site, the balloon is then expanded, for example, by injecting a fluid into the interior of the balloon. Expanding the balloon can expand the stenosis radially so that the vessel can permit an acceptable rate of fluid flow. After use, the balloon is collapsed, and the catheter is withdrawn.

SUMMARY

The invention relates to medical devices, such as medical balloons, and related methods. In some aspects, a medical balloon wall can have a void in its exterior surface. The void can be formed, for example, by ablation (e.g., laser ablation), and/or can be in the form of a groove. In embodiments, the void can form a void pattern in the balloon wall. The void can be filled with a material, such as a fiber or a nanomaterial (e.g., nanotubes, such as carbon nanotubes). In some embodiments, the void can be filled with a composite that includes a nanomaterial and, e.g., a polymer. In embodiments, the balloon exhibits enhanced burst pressure, profile and/or flexibility. In certain embodiments, the burst pressure of the balloon can be at least about 10 atm.

Embodiments may include one or more of the following advantages.

A balloon is provided that exhibits favorable burst pressure and flexibility characteristics. The addition of a nanomaterial into a void and/or an ablated region of a balloon can enhance the burst pressure of the balloon while maintaining the profile and/or flexibility of the balloon. In embodiments, a balloon that includes a nanomaterial in a void and/or an ablated region can have a relatively high burst pressure, good flexibility, and a relatively low profile. The nanomaterial can be relatively biocompatible. In some embodiments, the nanomaterial can deliver a therapeutic agent, drug, and/or pharmaceutically active compound to a target site within the body. A void or an ablated region can be formed in a balloon wall relatively quickly and easily. The void or ablated region can be formed to a relatively high degree of precision (e.g., in embodiments in which the void or ablated region is formed by laser ablation).

Still further aspects, features, and advantages follow.

DETAILED DESCRIPTION

Figure 1:
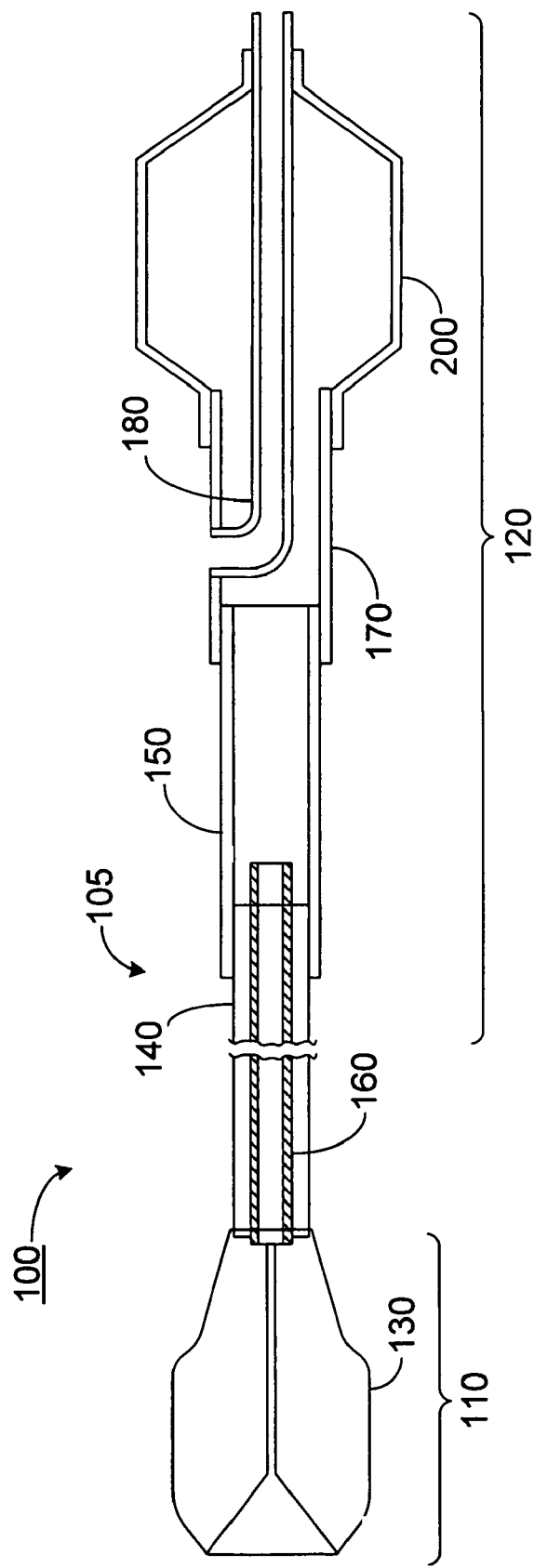
FIG. 1 is a cross-sectional side view of an embodiment of a balloon catheter.

Referring to FIG. 1, a rapid-exchange balloon catheter 100 includes a catheter shaft 105 having a proximal end 110 and a distal end 120, and a balloon 200 carried by the catheter shaft at the distal end. Catheter shaft 105 includes a proximal outer portion 150, a distal outer portion 170 connected to the proximal outer portion, and a distal inner portion 180 connected to the distal outer portion. At proximal end 110, balloon catheter 100 includes a manifold 130 connected to proximal outer portion 150 by a sheath 140 for a hypotube 160.

Balloon catheter 100 can be used as follows. An operator of balloon catheter 100 delivers distal end 120 of balloon catheter 100 into a body lumen (e.g., a blood vessel) over an emplaced guidewire. Manifold 130 can be used to control the positioning of distal end 120 of balloon catheter 100 in the body lumen. Balloon catheter 100 is navigated through the body lumen to position balloon 200 at a treatment site. Once balloon 200 reaches the treatment site, balloon 200 is inflated with inflation fluid, so that balloon 200 contacts the wall of the body lumen. Manifold 130 can be used to control the delivery of the inflation fluid to balloon 200. After balloon 200 has been inflated to contact the wall of the body lumen, balloon 200 is deflated and removed from the body lumen by withdrawing it, typically into an introducer sheath. Alternatively or additionally, balloon 200 can be used to deliver a medical device (e.g., a stent, a graft) and/or to block a passageway. Balloons and balloon catheters are described, for example, in Solar, U.S. Pat. No. 4,976,590, and Wang, U.S. Pat. No. 5,195,969. Stents are described, for example, in Heath, U.S. Pat. No. 5,725,570. The stent can include a coating, such as a drug elution layer.

Figure 2A:
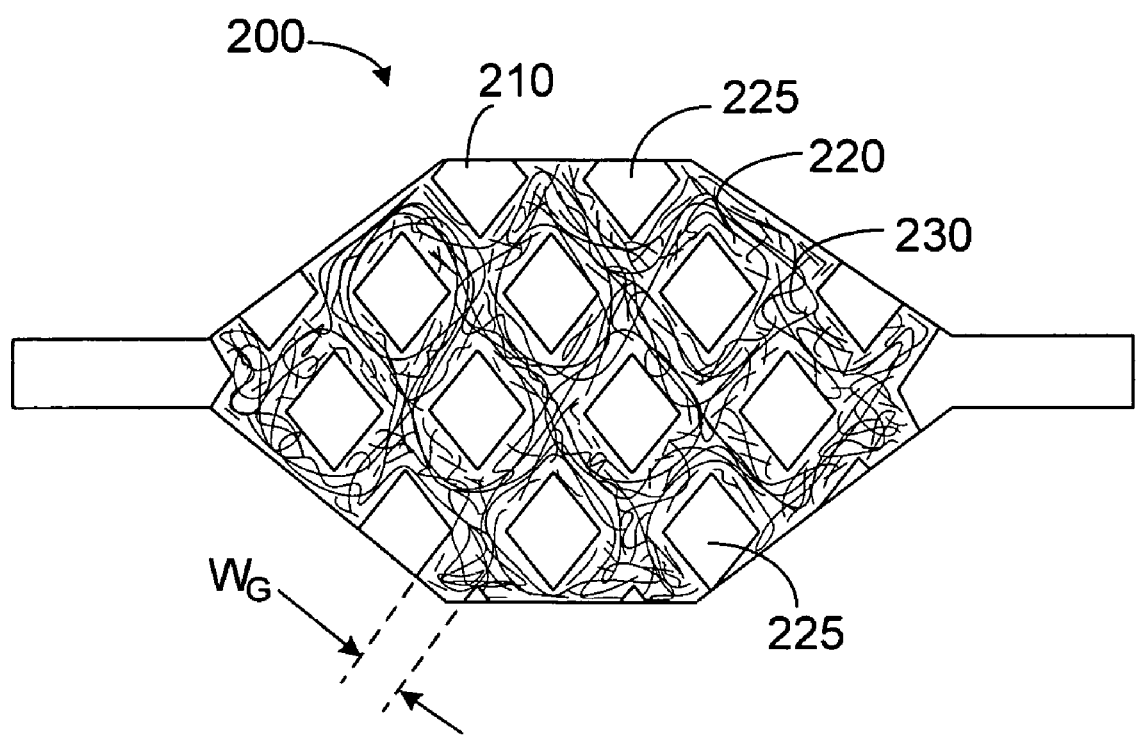
FIG. 2A is a side view of an embodiment of a medical balloon.
Figure 2B:
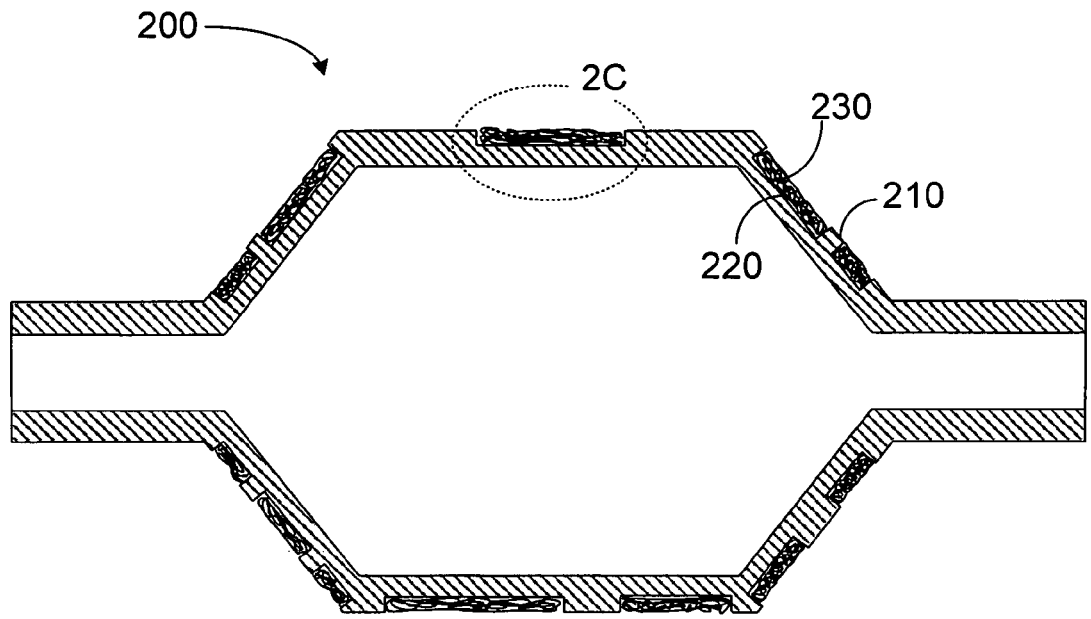
FIG. 2B is a cross-sectional side view of the medical balloon of FIG. 2A.
Figure 2C:
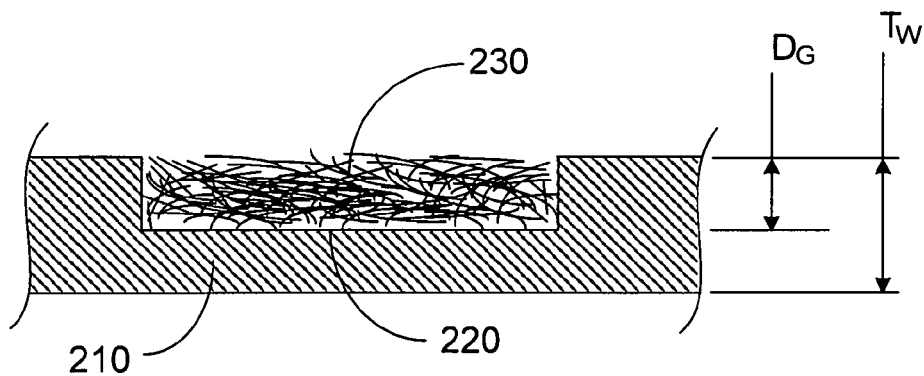
FIG. 2C is an enlarged view of region 2C in FIG. 2B.

Referring now to FIGS. 2A-2C, balloon 200 has a wall 210 with a pattern of grooves 220 formed in the balloon wall. A reinforcing material, particularly a nanomaterial 230, is disposed within grooves 220. The balloon exhibits favorable burst pressure and flexibility characteristics by combination of the balloon wall material, reinforcing material, and groove pattern. In embodiments, the balloon wall material is relatively soft and flexible; flexibility can be further enhanced by the groove pattern, which facilitates refolding and reduced withdrawal force. The reinforcing material is selected to enhance the burst pressure of the grooved balloon while maintaining improved flexibility. In other embodiments, the balloon wall includes a relatively nondistendible high burst material, such as a biaxially oriented polymer. The groove pattern can enhance flexibility of the balloon. The reinforcing material can maintain burst pressure and enhanced flexibility. In some embodiments, the burst pressure of the balloon is within about ±50% of the burst pressure of a similar balloon without a groove pattern and reinforcing material. In certain embodiments, the burst pressure of the balloon is within about ±20% (e.g., about ±10% or ±5%), of the burst pressure of a similar balloon without a groove pattern and reinforcing material.

Referring particularly to FIG. 2A and FIG. 2C, the groove is characterized by its pattern and dimensions. Referring particularly to FIG. 2A, a pattern of intersecting circumferential groove sections is illustrated which define a regular pattern of non-grooved land areas 225. This permits a reinforcing material to be supplied to the grooves in a pattern similar to a braid, which enhances flexibility along multiple axes relative to the balloon axis, and which can assist refolding during balloon deflation and can facilitate deflection or refolding when the deflated balloon encounters the body lumen or introducer sheath during withdrawal. The density of the pattern defines relatively small land areas 225 between the groove sections, which enhances the reinforcing function of the reinforcing material, thereby increasing burst pressure. In embodiments, groove sections can be non-intersecting, e.g. a continuous spiral or a double helix. Groove sections can be continuous or intermittent. The pattern can be asymmetric. Such asymmetric patterns may, for example, encourage deflation or refolding in a particular direction.

Wall 210 has a thickness "$T_W$" and groove 220 has a depth "$D_G$" and a width "$W_G$". Balloon flexibility is enhanced by increased groove depth and width. The specificity of deflection along a particular axis is enhanced by a narrower groove width. In embodiments, the ratio of groove width to depth is about 10 to 1 or less, e.g. about 1 to 1 or less. In embodiments, the groove depth can be at least about 1% of the balloon wall thickness, and/or about 95% or less of the balloon wall thickness (e.g., about 75% or less, about 25% or less, from about 5% to about 75%). In embodiments, the cross-sectional profile of the groove exhibits substantially vertical walls extending from a substantially planar floor, as illustrated. Alternatively, the profile is v-shaped or curved, e.g. hemispherical. The profile can be varied along the length of a groove.

In some embodiments, thickness "$T_W$" of wall 210 can be up to about 0.02 inch (e.g., from about 0.0003 inch to about 0.013 inch). Alternatively or additionally, depth "$D_G$" of groove 220 can be up to about 50 microns (e.g., from about 0.5 micron to about 25 microns). In certain embodiments, width "$W_G$" of groove 220 can be up to about 1500 microns (e.g., from about one micron to about 1000 microns). In embodiments, at least one of the dimensions of groove 220 (e.g., depth "$D_G$", width "$W_G$") can be nano-sized (less than about 1000 nm). For example, depth "$D_G$" and/or width "$W_G$" can be less than about 750 nm (e.g., less than about 500 nm).

The reinforcing material is selected for its reinforcing characteristics, e.g. its ability to enhance burst pressure in the pattern defined by the grooves, and its flexibility. Particularly, the reinforcing material includes nanomaterials. Nanomaterial 230 includes particles and/or fibers having at least one dimension less than about 1000 nm. In some embodiments, nanomaterial 230 can include nanotubes. The nanotubes can be, for example, single-walled nanotubes (SWNT) or multi-walled nanotubes (MWNT). In some embodiments, the nanotubes can be double-walled nanotubes (DWNT). Examples of nanotubes include carbon nanotubes, such as hollow carbon nanotubes (e.g., hollow single walled carbon nanotubes, hollow multiwalled carbon nanotubes (sometimes called buckytubes)); ceramic nanotubes, such as boron nitride nanotubes and aluminum nitride nanotubes; and metallic nanotubes, such as gold nanotubes. Carbon nanotubes are available from, for example, Rice University. Synthesis of carbon nanotubes is described, for example, in Bronikowski et al., *J. Vac. Sci. Technol.* A, 19(4), 1800-1805 (2001); and Davis et al., *Macromolecules* 2004, 37, 154-160. Boron nitride nanotubes are available from the Australian National University (Canberra, Australia). In certain embodiments, nanomaterial 230 can include more than one type of nanotube. Nanomaterial 230 can be positively or negatively charged, or can be neutral. Nanomaterial 230 can include one or more metals or metal alloys, such as stainless steel. In some embodiments, nanomaterial 230 can include one or more polymers, such as high-density polyethylene (HDPE). In certain embodiments, nanomaterial 230 can include a nanoclay, such as montmorillonite clay. Nanomaterials are described, for example, in commonly assigned U.S. Ser. No. 10/850,087, filed on May 20, 2004, and entitled "Medical Devices", which is incorporated herein by reference in its entirety.

In some embodiments, nanomaterial 230 can be bonded to balloon 200 by one or more other materials. For example, nanomaterial 230 can be bonded to balloon 200 by an adhesive, such as a UV-curable acrylate resin. In certain embodiments, nanomaterial 230 can be dispersed in a polymer to form a polymer composite that is then bonded to balloon 200. Examples of suitable polymers are provided infra with reference to the balloon wall material. In embodiments in which nanomaterial 230 is dispersed in a polymer to form a polymer composite, the polymer composite can further include one or more additives that enhance formation of the composite. For example, the polymer composite can include one or more coupling or compatibilizing agents, dispersants, stabilizers, plasticizers, surfactants, and/or pigments, that enhance interactions between the nanomaterial and the polymer(s). Examples of additive(s) are described in U.S. Patent Application Publication No. US 2003/0093107, published on May 15, 2003, which is incorporated herein by reference.

In some embodiments, nanomaterial 230 can be modified to enhance interactions between the components of the nanomaterial and/or between the nanomaterial and other materials. As an example, in embodiments in which nanomaterial 230 includes nanotubes, the nanotubes can be modified to enhance interactions between the nanotubes and a polymer in wall 210 of balloon 200. As another example, the nanotubes can be modified to enhance interactions between the nanotubes and a polymer within which the nanotubes are dispersed. For example, the nanotubes can be chemically modified with one or more functional groups that increase interactions (e.g., compatibility) between the nanotubes and the polymer. Functionalization of carbon nanotubes is described, for example, in Bahr et al., *J. Am. Chem. Soc.* 2001, 123, 6536-6542, and in U.S. Patent Application Publication No. US 2003/0093107, published on May 15, 2003, both of which are incorporated herein by reference. Alternatively or additionally, nanotubes can be connected or crosslinked, for example, by irradiation. Irradiation of carbon nanotubes is described, for example, in Krasheninnikov et al., *Phys. Rev. B* 66, 245403 (2002); and in commonly assigned U.S. Ser. No. 10/850,085, filed on May 20, 2004, and entitled "Medical Devices and Methods of Making the Same", both of which are incorporated herein by reference in their entirety.

In particular embodiments, the reinforcing material fills the grooves. As shown in FIGS. 2B and 2C, nanomaterial 230 fills grooves 220, such that the profile of balloon 200 is generally smooth. In other embodiments, the nanomaterial does not fill the groove or overfills the groove to provide a morphology on the balloon surface. A morphology on the exterior surface can, e.g. aid stent retention during delivery.

Balloon 200 (e.g., wall 210 of balloon 200) can include, for example, one or more polymers (e.g., a mixture of polymers). For example, balloon 200 can include one or more thermoplastics and/or thermosets. Examples of thermoplastics include polyolefins; polyamides (e.g., nylon, such as nylon 12, nylon 11, nylon 6/12, nylon 6, nylon 66); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; fluoropolymers; copolymers and block copolymers thereof, such as block copolymers of polyether and polyamide (e.g., PEBAX®); and mixtures thereof. Examples of thermosets include elastomers (e.g., EPDM), epichlorohydrin, polyureas, nitrile butadiene elastomers, and silicones. Other examples of thermosets include epoxies and isocyanates. Biocompatible thermosets may also be used. Biocompatible thermosets include, for example, biodegradable polycaprolactone, poly(dimethylsiloxane) containing polyurethanes and ureas, and polysiloxanes. Ultraviolet curable polymers, such as polyimides, can also be used. Other examples of polymers that can be used in balloon 200 include polyethylenes, polyethylene ionomers, polyethylene copolymers, polyetheretherketone (PEEK), thermoplastic polyester elastomers (e.g., Hytrel®)), and combinations thereof. The balloon can include multiple layers provided, e.g., by coextrusion. Other polymers are described, for example, in commonly assigned U.S. Ser. No. 10/645,055, filed on Aug. 21, 2003, and entitled "Medical Balloons", which is incorporated herein by reference.

In embodiments, balloon 200 can have a burst pressure of at least about 5 to 10 atm (e.g., about 10 atm or greater). In certain embodiments, balloon 200 can have a burst pressure of up to about 30 atm or up to about 40 atm. As referred to herein, the burst pressure of a balloon refers to the internal pressure at which the balloon bursts. One way the burst pressure of a balloon is determined is by measuring the internal pressure of the balloon as the balloon is inflated at a rate of two psi per second with a 10 second hold at every 50 psi interval until the balloon bursts.

In particular embodiments, the balloon includes a semi-distendible (semi-compliant) polymer, and has a groove pattern with a nanomaterial reinforcing material. Compared to a similar balloon without grooves or nanomaterial, the balloon exhibits increased burst pressure and a comparable flexibility. In particular embodiments, the balloon includes a substantially nondistendible (non-compliant) polymer, and has a groove pattern with nanomaterial. Compared to a similar balloon without grooves or nanomaterial, the balloon exhibits comparable or improved burst pressure and improved flexibility. In particular embodiments, the balloon is sized for use in the vascular system, e.g. the coronary arteries. In other embodiments, the balloon is configured for use in other body lumens such as the GI tract. In some embodiments, the balloon can be configured for use in urological (e.g., urinary) applications.

In some embodiments, a balloon parison can be formed and then stretched and inflated to form a balloon precursor, and grooves 220 can thereafter be ablated into the wall of the balloon precursor. In certain embodiments, a balloon parison can be formed, and grooves 220 can be ablated into the surface of the parison. Then, the balloon parison can be stretched and expanded to form a balloon precursor. After the balloon precursor has been formed, the grooves 220 can be filled with nanomaterial 230.

A balloon can be formed using any suitable technique, such as blow molding, film molding, injection molding, and/or extrusion. For example, a polymer tube can be extruded, and can thereafter be stretched and blown to form a balloon. Methods of making medical tubing are described, for example, in commonly assigned U.S. Patent Application Publication No. US 2004/0078052 A1, published on Apr. 22, 2004, which is incorporated herein by reference. Methods of forming a balloon from a tube are described, for example, in commonly-assigned U.S. Ser. No. 10/263,225, filed Oct. 2, 2002, and entitled "Medical Balloon"; Anderson, U.S. Pat. No. 6,120,364; Wang, U.S. Pat. No. 5,714,110; and Noddin, U.S. Pat. No. 4,963,313, all incorporated herein by reference in their entirety. After it has been formed, balloon 200 can be attached to catheter shaft 105 by, for example, laser bonding. Other attachment methods are described, for example, in references incorporated herein. Catheter shaft 105 may also be any of the multilayer tubes described in commonly assigned U.S. Ser. No. 10/645,014, filed Aug. 21, 2003, which is incorporated herein by reference.

Grooves 220 can be formed, for example, by laser ablation. Laser ablation of balloons is described, for example, in commonly assigned U.S. patent application Ser. No. 11/060,151, filed concurrently with this application, which is incorporated herein by reference.

Figure 3A:
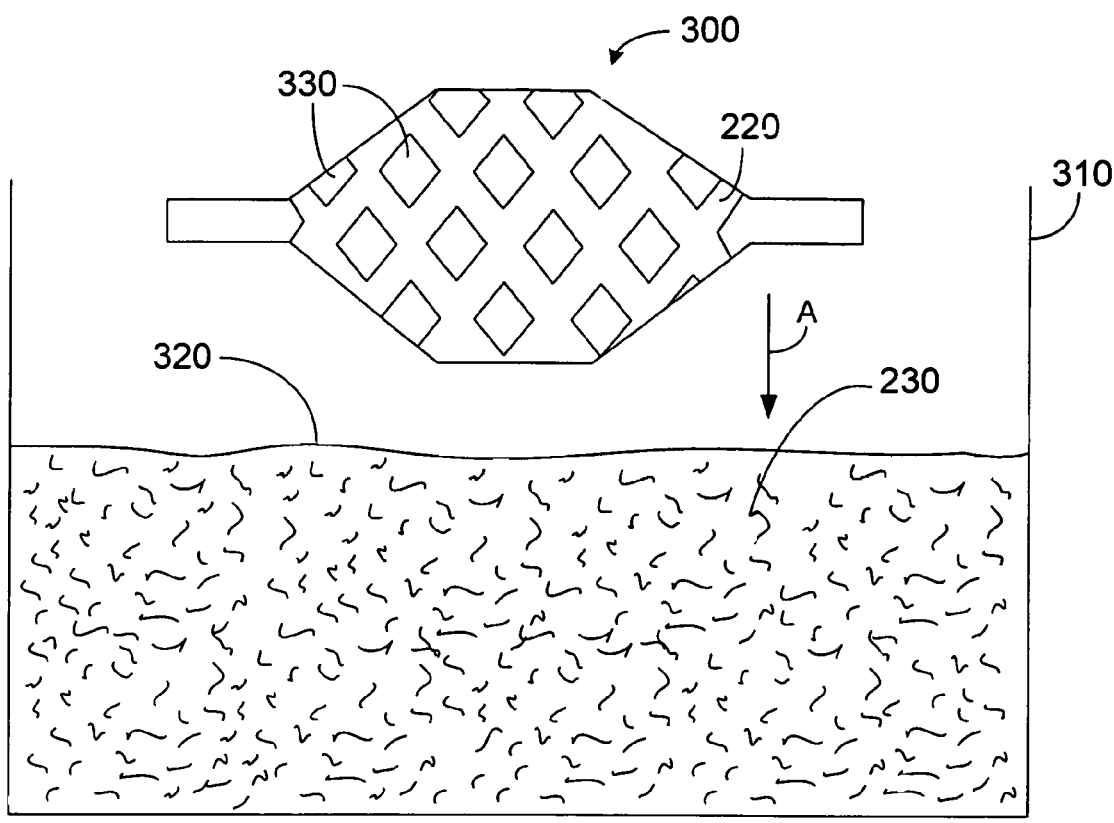
FIGS. 3A and 3B illustrate a process for forming the medical balloon of FIGS. 2A and 2B.
Figure 3B:
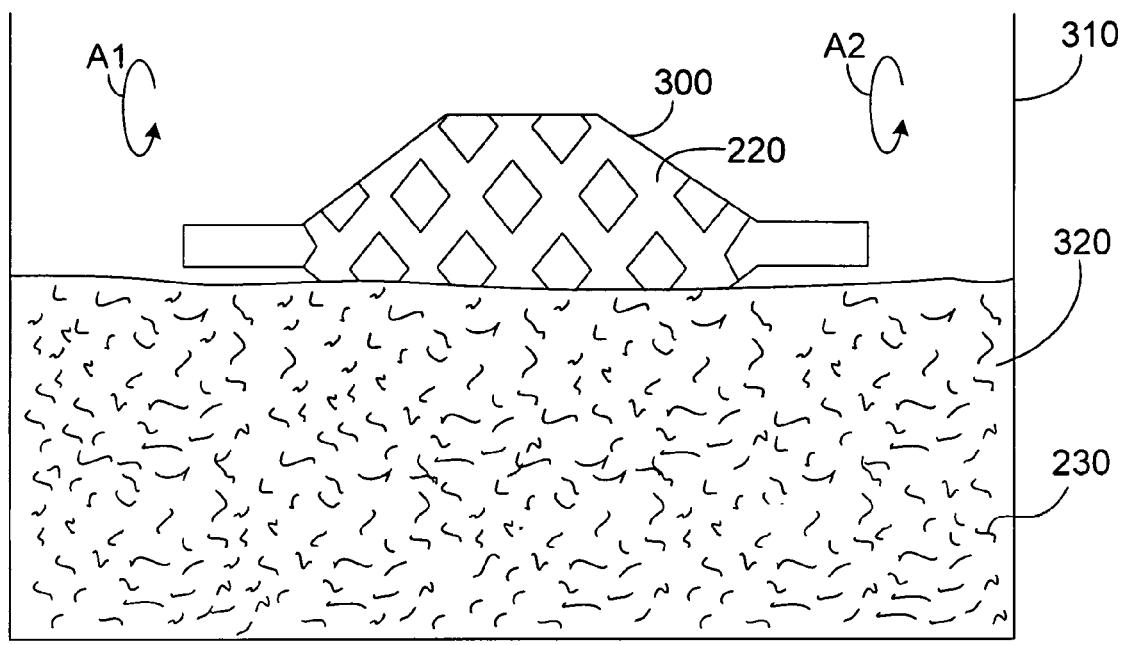

FIGS. 3A and 3B illustrate a method for filling grooves 220 with nanomaterial 230. In FIGS. 3A and 3B, a balloon precursor 300, which includes grooves 220, is moved (in the direction of arrow "A") toward a vat 310 that includes a solvent 320 and a nanomaterial 230 dispersed within the solvent. Solvent 320 can be, for example, water or a polymer (e.g., a polysaccharide, a polyvinyl alcohol). As FIG. 3B shows, once balloon precursor 300 is partially submerged in solvent 320, balloon precursor 300 is rotated in solvent 320 (in the direction of arrows A1 and A2), so that nanomaterial 230 attaches to balloon precursor 300. Solvent 320 facilitates the application of nanomaterial 230 to balloon precursor 300. After balloon precursor 300 has been fully rotated in solvent 320, balloon precursor 300 is removed from solvent 320. Thereafter, excess nanomaterial (nanomaterial that is not within grooves 220) is removed from balloon precursor 300 by, for example, one or more wipers that wipe off the surface of balloon precursor 300. Alternatively or additionally, excess nanomaterial can be removed from balloon precursor 300 by pulling balloon precursor 300 through a die. At the end of the process, balloon 200 has been formed.

In some embodiments, the outer surface of balloon precursor 300 is covered by a removable layer, such as a wax layer. Grooves 220 are then formed through the removable layer into the balloon wall. While grooves 220 are not covered by the wax layer, the land areas 330 that are formed between the grooves are covered by the wax layer. Balloon precursor 300 is then dipped into solvent 320, such that nanomaterial 230 fills grooves 220 and covers land areas 330. Thereafter, balloon precursor 300 is removed from solvent 320, and the wax is removed (e.g., by peeling the wax off of land areas 330 or by solvating the wax) to produce balloon 200.

Alternatively or additionally, in embodiments in which nanomaterial 230 is charged, balloon precursor 300 can be charged (e.g., via plasma treatment). Thereafter, a charged polyelectrolyte (e.g., poly(ethyleneimine)) can be layered onto balloon precursor 300 (e.g., into grooves 220). Balloon precursor 300 can then be exposed to, for example, charged nanotubes (e.g., in a solvent) that can attach to the charged sections of balloon precursor 300. In some embodiments, another polyelectrolyte layer can be added to balloon precursor 300, and can be followed by the addition of another nanotube layer. This layering can continue as desired. After a suitable amount of nanomaterial 230 has been added to balloon precursor 300, a curing agent (e.g., glutaraldehyde) can be used to cure the nanomaterial and polyelectrolyte layer(s). Polyelectrolyte layering processes are described, for example, in U.S. patent application Ser. No. 10/849,742, filed on May 20, 2004, and entitled "Medical Devices Having Multiple Layers", and in *Nature Materials*, Vol. 1 (November 2002), 190-194, both of which are incorporated herein by reference.

In embodiments, nanomaterial 230 can be added to grooves 220 of balloon precursor 300 via hydrophilic and/or hydrophobic interactions between the nanomaterial and the grooves. For example, both the nanomaterial and the grooves can be hydrophilic, while land areas 330 of balloon precursor 300 are hydrophobic, such that the nanomaterial may be attracted to the grooves and repelled by the land areas. As a result, the nanomaterial may fill the grooves without also coating the land areas. In some embodiments, both the nanomaterial and the grooves can be hydrophobic, while the land areas are hydrophilic, such that the nanomaterial may fill the grooves without also coating the land areas.

In certain embodiments, balloon precursor 300 can be functionalized (e.g., via a chemical reaction) as the balloon precursor is being ablated. For example, a reactive gas (e.g., plasma gas) can be introduced into grooves 220 as the grooves are being formed by ablation. The reactive gas can, e.g., cause the grooves to become charged, and to thereby attract a charged nanomaterial.

Nanomaterial 230 may be inherently hydrophilic or hydrophobic, or can be rendered hydrophilic or hydrophobic by, for example, chemical modification, such as the addition of one or more functional groups to the nanomaterial (described supra). Alternatively or additionally, the nanomaterial may be dispersed in a hydrophilic or hydrophobic solvent that can then be used to deliver the nanomaterial to the corresponding hydrophilic or hydrophobic groove(s) in the balloon precursor. In embodiments, grooves 220 and/or land areas 330 of balloon precursor 300 can be formed of, for example, a polymer. The polymer may be inherently hydrophilic or hydrophobic, or may be rendered hydrophilic or hydrophobic via the addition of one or more functional groups. Examples of hydrophilic functional groups include hydroxyl groups, carbonyl groups, carboxyl groups, and carboxylate groups. Examples of hydrophobic functional groups include hydrocarbons, silicones, and fluorocarbons. In certain embodiments, the land areas and/or grooves of the balloon precursor may be selectively coated with a hydrophilic or hydrophobic coating (e.g., a hydrophilic polymer coating, such as poly (hydroxyethyl methacrylate) or polyethylene oxide). For example, the land areas can be covered with a protective layer (e.g., a wax layer) such that the grooves can be coated without also coating the land areas. After the grooves have been coated, the protective layer can be removed from the land areas. Methods for making polymers and/or nanomaterials hydrophilic or hydrophobic are described, for example, in Richard J. LaPorte, *Hydrophilic Polymer Coatings for Medical Devices* (Technomic Publishing Co., Inc., 1997), and in Velasco-Santos et al., "Improvement of Thermal and Mechanical Properties of Carbon Nanotube Composites Through Chemical Functionalization", *Chem. Mater.* 15 (2003), 4470-4475, both of which are incorporated herein by reference.

Other methods of attaching nanomaterial 230 to balloon precursor 300 include spraying. In some embodiments, a mixture containing nanotubes and a solvent (e.g., 1,1,2,2-tetrachloroethane) can be sprayed onto balloon precursor 300 to form balloon 200. The solvent can evaporate, resulting in a layer of nanotubes, sometimes called bucky paper, on the surface of the balloon (e.g., in grooves 220).

Figure 4:
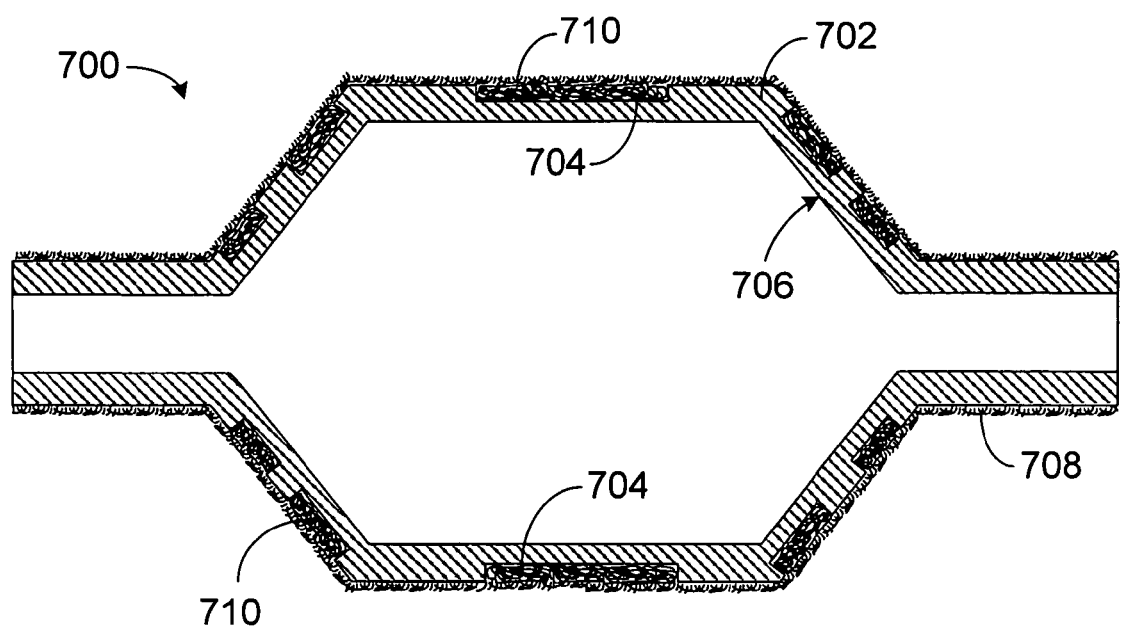
FIG. 4 is a cross-sectional side view of an embodiment of a medical balloon.

While methods of adding a nanomaterial into the grooves of a balloon precursor without also adding the nanomaterial into the land areas of the balloon precursor have been described, in certain embodiments, a nanomaterial can be added into both the grooves and the land areas of a balloon precursor. For example, a balloon precursor with grooves and land areas can be sprayed with a nanomaterial solution, such that the nanomaterial solution both fills the grooves and coats the land areas. As an example, FIG. 4 shows a balloon 700 that has a wall 702 with a pattern of grooves 704 formed in the balloon wall. Wall 702 has an interior surface 706 and an exterior surface 708. Nanomaterial 710 covers exterior surface 708 of wall 702, and fills grooves 704. While not shown, in some embodiments, the thickness of a nanomaterial layer on a balloon surface can vary in different regions of the balloon surface. For example, one region of a balloon surface can have a thicker layer of nanomaterial disposed on it than another region of the balloon surface.

While certain embodiments have been described, other embodiments are possible.

As an example, while a single-layer balloon has been shown, in some embodiments, a balloon that includes an ablated region can be a multilayer balloon. For example, the balloon can have two, three, four, five, or six layers. A multilayer balloon can be formed by, for example, coextrusion. In certain embodiments in which the balloon is a multilayer balloon (e.g., a balloon having five layers), the ablated region may extend into only the top layer or the top two layers of the balloon.

As an additional example, in some embodiments, a balloon can include more than one type and/or size of nanomaterial. For example, a groove in the balloon can include both carbon nanotubes and ceramic nanotubes. In certain embodiments, the balloon can be formed of a polymer composite including one type of nanomaterial, and a groove in the balloon wall can be filled with another type of nanomaterial.

As a further example, in certain embodiments, a nanomaterial (such as nanotubes) that is combined with chitosan, chondroitin, and/or DNA can be added to a balloon or balloon precursor.

Figure 5:
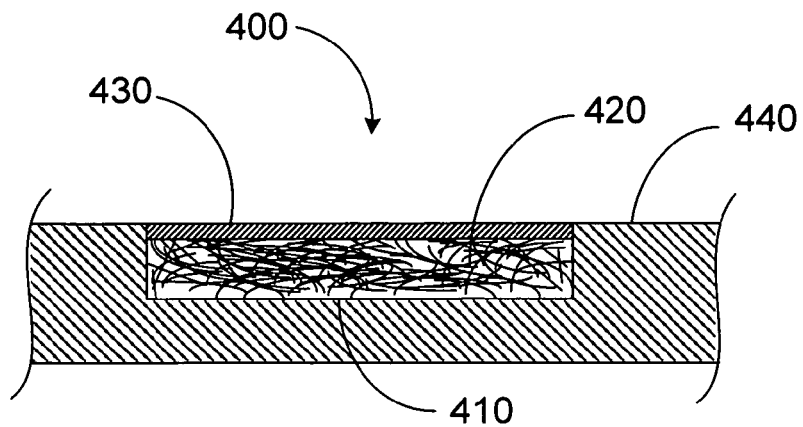
FIG. 5 is a cross-sectional side view of a region of an embodiment of a medical balloon.
Figure 6:
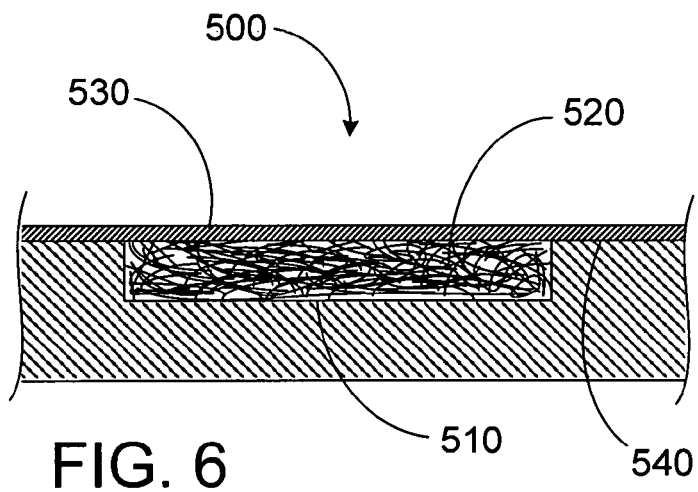
FIG. 6 is a cross-sectional side view of a region of an embodiment of a medical balloon.
Figure 7:
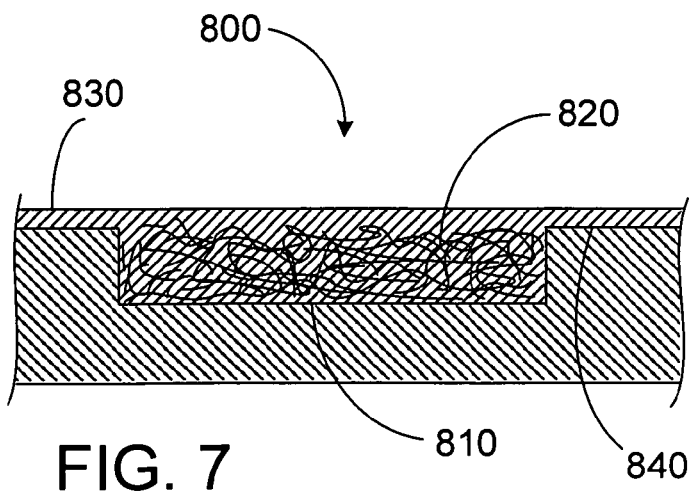
FIG. 7 is a cross-sectional side view of a region of an embodiment of a medical balloon.

In certain embodiments, and referring now to FIGS. 5-7, a groove in a balloon wall can be filled with a nanomaterial and then covered with a protective layer. For example, FIG. 5 shows a balloon wall 400 with a groove 410, and nanomaterial 420 filling the groove. A protective layer 430 covers groove 410, and is flush with surface 440 of balloon wall 400. As another example, FIG. 6 shows a balloon wall 500 with a groove 510 that is filled with nanomaterial 520. A protective layer 530 covers both groove 510 and surface 540 of balloon wall 500. In some embodiments, a balloon can include a protective layer that fills a portion or all of a groove in a wall of the balloon. For example, FIG. 7 shows a balloon wall 800 with a groove 810, and a nanomaterial 820 filling the groove. A protective layer 830 covers both groove 810 and surface 840 of balloon wall 800, while also filling groove 810. Protective layers 430, 530, and 830 can be formed, for example, from one or more polymers, such as elastomers, modified UV-curable polyester acrylate resins (e.g., acrylate/acetoacetate synthesized by a Michael reaction), polyurethanes, and/or polyethers. In some embodiments, a protective layer can be formed of a UV-curable (e.g., UV-crosslinkable) polymer (e.g., a polyester) that, when cured by ultraviolet radiation, can enhance bonding of the nanomaterial to the grooves of the balloon. While not shown, in some embodiments, a protective layer such as polyurethane can cover substantially all of the outer surface of a balloon. Other examples of materials that can be used in a protective layer include polymers such as Pebax®, Hytrel®, and polyisobutylene-polystyrene block copolymers (e.g., styrene-isobutylene-styrene). Polymers are described, for example, in Pinchuk et al., U.S. Pat. No. 6,545, 097, which is incorporated herein by reference. In some embodiments in which the balloon includes a protective layer, the material filling the grooves in the balloon may not be biocompatible. In such embodiments, the protective layer can protect the body from exposure to the non-biocompatible material. In certain embodiments in which the balloon includes a protective layer, the material filling the grooves may be water-soluble. In such embodiments, the protective layer can prevent the water-soluble material from dissolving upon contact with, for example, blood.

As another example, in some embodiments, a nanomaterial can be added to a balloon by dissolving the nanomaterial in a solvent to form a solution, and then applying the solution to the balloon. The solution can be applied to the balloon by, for example, injection through a syringe. In certain embodiments, some of the water can be removed from the solution (e.g., by evaporation) to form a gel, and the gel can be applied to the balloon. A carbon nanotube solution can be formed, for example, by dissolving carbon nanotubes in water using arabic gum. Suitable carbon nanotube-arabic gum solutions are described, for example, in R. Bandyopadhyaya et al., "Stabilization of Individual Carbon Nanotubes in Aqueous Solutions", *Nano Letters*, 2 (2002), 25-28, which is incorporated herein by reference. In some embodiments, a carbon nanotube solution can be formed by dissolving carbon nanotubes in water using polymer-wrapping techniques, such as those described in Michael J. O'Connell et al., "Reversible Water-Solubilization of Single-Walled Carbon Nanotubes by Polymer Wrapping", *Chem. Phys. Letters* 342 (2001), 265-271, which is incorporated herein by reference. In certain embodiments, a nanotube solution can be made by adding nanotubes (e.g., single-walled nanotubes (SWNT)) into a surfactant (e.g., 1% by weight aqueous sodium dodecyl sulfate (SDS)), homogenizing the resulting mixture for about one hour (e.g., at about 6500 revolutions per minute), and then sonicating the mixture (e.g., for about 10 minutes). The resulting solution can be applied to a balloon by, for example, spraying the solution onto the balloon (e.g., using an ultrasonic nozzle, such as a MicroMist system from Sono-Tek). In some embodiments, methanol can also be sprayed onto the balloon to help remove the surfactant from the nanotubes and thereby drive the nanotubes out of solution and onto the balloon surface. The formation and casting of nanotube solutions is described, for example, in A. Meitl et al., "Solution Casting and Transfer Printing Single Walled Carbon Nanotube Films", *Nano Letters* 4:9 (2004), 1643-1747, which is incorporated herein by reference.

As an additional example, in some embodiments, nanomaterial (e.g., nanotubes) can be applied to a balloon or balloon precursor using a picoliter dispenser, such as a picoliter dispenser from Microdrop GmbH (Germany). In certain embodiments, a solution including nanomaterial can be added onto a balloon or balloon precursor using a picoliter dispenser.

As a further example, in certain embodiments, a balloon that includes one or more ablated regions can include a fiber that is wound through the ablated region(s). In some embodiments, the fiber can include nanomaterial (e.g., nanotubes) within it (e.g., for reinforcement). The fiber can allow high loading (e.g., up to about 50% by weight) of nanomaterial on the balloon. Nanotube-containing fibers can be formed, for example, by electrospinning, described in Ko et al., *Adv. Mater.* 2000, 15, No. 14, Jul. 17, 1161-1163; and "Carbon Nanotube Reinforced Carbon Nano Composite Fibrils By Electro-Spinning", thesis by Ashraf Abd El-Fattah Ali, Drexel University, October 2002. In certain embodiments, the fiber may not contain any nanomaterial in it. The fiber can be, for example, a long, continuous fiber that is not nano-sized and that does not include any nanomaterial in it. In such embodiments, the balloon may or may not contain nanomaterials (e.g., in the same groove in which the fiber is wound). In some embodiments, a fiber can include one or more polymers, such as ultra-high molecular weight polyethylene, polyesters, and polymeric aromatic amides (e.g., Kevlar®, available from DuPont). In certain embodiments, a fiber can include spider silk; in some such embodiments, the fiber can be substantially formed of spider silk.

In certain embodiments, one or more fibers can be added to a balloon or a balloon precursor by electrospinning. For example, a carbon fiber can be electrospun onto the surface (e.g., into a groove) of a balloon. In some embodiments, a fiber can be electrospun into one or more grooves in a balloon, and the balloon can thereafter be disposed within a mold. Heat and/or internal pressure can then be applied to the balloon, to help attach or integrate the fiber into the groove. Electrospinning is described, for example, in Zheng-Ming Huang et al., "A Review on Polymer Nanofibers by Electrospinning and Their Applications in Nanocomposites", *Composites Science and Technology* 63 (2003), 2223-2253, and in Sian F. Fennessey et al. and Richard J. Farris, "Fabrication of Aligned and Molecularly Oriented Electrospun Polyacrylonitrile Nanofibers and the Mechanical Behavior of Their Twisted Yarns", *Polymer* 45 (2004), 4217-4225, both of which are incorporated herein by reference. In certain embodiments, one or more therapeutic agents and/or pharmaceutically active compounds (such as those described below) can be incorporated (e.g., embedded) into one or more fibers that are electrospun onto a balloon or balloon precursor. In certain embodiments, one or more fibers can be electrospun onto a balloon and/or balloon precursor from a solution that includes one or more therapeutic agents and/or pharmaceutically active compounds. As a result, the fibers that are electrospun onto the balloon and/or balloon precursor can include the therapeutic agent(s) and/or pharmaceutically active compound(s). In some embodiments, the electrospun fibers can be porous, and/or can be made out of a biodegradable material, such that the electrospun fibers can release a therapeutic agent and/or pharmaceutically active compound during use (e.g., through the pores in the fibers and/or as the biodegradable material biodegrades).

As another example, in some embodiments, a balloon can include one or more nanocomposites. For example, a balloon can include one or more grooves that are filled with a nanocomposite. Nanocomposites are described, for example, in Parsonage et al., U.S. Patent Application Publication No. US 2003/0093107 A1, published on May 15, 2003, which is incorporated herein by reference.

As an additional example, in certain embodiments, a balloon can include one or more grooves that are randomly located on the balloon surface (i.e., that do not form a pattern on the balloon surface). In certain embodiments, one or more of the grooves can be filled with, for example, a nanomaterial and/or a fiber. Alternatively or additionally, a balloon can include grooves that have different thicknesses and/or widths.

In some embodiments, one or more of the nanomaterials in a balloon can include, or can be modified to include, a therapeutic agent (e.g., a drug) or a pharmaceutically active compound. As an example, certain ceramics are relatively porous. Thus, a therapeutic agent can be loaded onto ceramic nanotubes by, for example, dipping or soaking the ceramic nanotubes in a solution containing the therapeutic agent, and allowing the therapeutic agent to diffuse through the pores. Suitable ceramic materials are described, for example, in U.S. Ser. No. 10/762,816, filed on Jan. 22, 2004, and entitled "Medical Devices", which is incorporated herein by reference. As another example, a nanomaterial (e.g., nanoparticles) can be coated (e.g., spray-coated) with one or more therapeutic agents. In embodiments in which the balloon includes a protective layer, the protective layer can also serve as a diffusion layer that can, for example, regulate the diffusion of therapeutic agent out of the balloon. Therapeutic agents and pharmaceutically active compounds are described, for example, in Phan et al., U.S. Pat. No. 5,674,242; U.S. Patent Application Publication No. US 2003/0185895 A1, published on Oct. 2, 2003; U.S. Patent Application Publication No. US 2003/0003220 A1, published on Jan. 2, 2003; and U.S. Patent Application Publication No. US 2003/0018380 A1, published on Jan. 23, 2003. Examples of therapeutic agents and pharmaceutically active compounds include anti-thrombogenic agents, thrombogenic agents, antioxidants, anti-inflammatory agents, anesthetic agents, anti-coagulants, anti-restenosis agents, thrombosis agents, immunosuppressant agents, and antibiotics. In some embodiments, a balloon can include more than one type of therapeutic agent and/or pharmaceutically active compound. For example, the balloon can include a first nanomaterial including one type of therapeutic agent, and a second nanomaterial including another type of therapeutic agent.

While a rapid-exchange catheter has been described, in certain embodiments, a catheter that includes one of the above-described balloons can be a different type of rapid-exchange catheter, or can be a single-operator exchange catheter or an over-the-wire catheter. Single-operator exchange catheters are described, for example, in Keith, U.S. Pat. No. 5,156,594, and in Stivland et al., U.S. Pat. No. 6,712,807, both of which are incorporated herein by reference. Over-the-wire catheters are described, for example, in commonly assigned U.S. Patent Application Publication No. US 2004/0131808 A1, published on Jul. 8, 2004, which is incorporated herein by reference. In some embodiments, a catheter that includes one of the above-described balloons can be a fixed-wire catheter. Fixed-wire catheters are described, for example, in Segar, U.S. Pat. No. 5,593,419, which is incorporated herein by reference.

While not shown, in certain embodiments, a balloon that includes one or more ablated regions that are filled or partially filled with a nanomaterial can be an over-the-wire balloon or a fixed-wire balloon, and/or can include one or more cutting elements. Over-the-wire balloons are described, for example, in Solar, U.S. Pat. No. 4,976,590, which is incorporated herein by reference. Fixed-wire balloons are described, for example, in Segar, U.S. Pat. No. 5,593,419, incorporated supra. Balloons with cutting elements are described, for example, in U.S. Patent Application Publication No. US 2003/0163148 A1, published on Aug. 28, 2003; U.S. Patent Publication No. US 2004/0133233 A1, published on Jul. 8, 2004; and U.S. Ser. No. 10/744,507, filed on Dec. 22, 2003, and entitled "Medical Device Systems", all of which are incorporated herein by reference.

In some embodiments, a balloon parison or balloon precursor can be coated with nanomaterial prior to being formed into a balloon. Thereafter, the balloon parison or balloon precursor can be formed into a balloon.

All publications, applications, references, and patents referred to above are incorporated by reference in their entirety.

Other embodiments are within the scope of the following claims.

What is claimed is:

1. A medical device, comprising:
    an inflatable balloon having a wall with an interior surface and an exterior surface defining a wall thickness therebetween;
    a pattern formed within the exterior surface of the balloon, the pattern comprising a plurality of intersecting grooves intersecting at a plurality of intersection points and forming a plurality of non-grooved land areas; and
    a coating disposed within and filling the pattern such that the coating surrounds a perimeter of at least some of the land areas;
    wherein at least some of the plurality of grooves have a width to depth ratio that is about 10:1 or less; and
    the coating comprises a nanomaterial.

2. The medical device of claim 1, wherein the plurality of grooves have a depth that is from about 5% to about 75% of the thickness of the wall.

3. The medical device of claim 1, wherein the nanomaterial comprises a plurality of nanotubes.

4. The medical device of claim 1, wherein the nanomaterial comprises a fiber including a nanomaterial.

5. The medical device of claim 1, wherein the nanomaterial is disposed in a matrix polymer.

6. The medical device of claim 1, wherein the pattern is filled to a depth level with the exterior surface of the wall.

7. The medical device of claim 1, wherein the pattern is filled to a depth that is less than or greater than the exterior surface of the wall.

8. The medical device of claim 1, wherein the balloon has a burst pressure of at least about 10 atm.

9. The medical device of claim 1, wherein the balloon is formed of a biaxially oriented material.

10. The medical device of claim 1, wherein the balloon is formed of a polymer selected from PEBAX, PET, PEN, PBT, PEEK, Hytrel, polyurethane, or nylon.

11. The medical device of claim 1, further comprising a second coating disposed over the nanomaterial and the land areas.

12. The medical device of claim 1, further comprising a second coating disposed over the nanomaterial such that the second coating is level with a top surface of the land areas.

13. The medical device of claim 1, wherein the coating is further disposed over at least some of the land areas.

14. The medical device of claim 1, further comprising a stent.

15. The medical device of claim 14, wherein the stent includes a drug.

* * * * *